(12) United States Patent
Kumata (10) Patent No.: US 11,872,081 B2
(45) Date of Patent: Jan. 16, 2024

(54) ULTRASOUND TRANSDUCER, ULTRASOUND ENDOSCOPE, AND MANUFACTURING METHOD OF ULTRASOUND TRANSDUCER

(71) Applicant: OLYMPUS CORPORATION, Tokyo (JP)

(72) Inventor: Yuya Kumata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 193 days.

(21) Appl. No.: 17/410,466

(22) Filed: Aug. 24, 2021

(65) Prior Publication Data

US 2021/0378635 A1 Dec. 9, 2021

Related U.S. Application Data

(63) Continuation of application No. PCT/JP2019/014268, filed on Mar. 29, 2019.

(51) Int. Cl.
*A61B 8/00* (2006.01)
*B06B 1/02* (2006.01)
*B06B 1/06* (2006.01)
*A61B 8/12* (2006.01)

(52) U.S. Cl.
CPC .......... *A61B 8/4494* (2013.01); *B06B 1/0215* (2013.01); *B06B 1/06* (2013.01); *A61B 8/12* (2013.01)

(58) Field of Classification Search
CPC .................................................. A61B 8/12
See application file for complete search history.

(56) References Cited

U.S. PATENT DOCUMENTS

| 5,795,299 A * | 8/1998 | Eaton ........................ A61B 8/12 600/459 |
| 7,336,446 B2 | 2/2008 | Kanagawa |
| 8,059,369 B2 | 11/2011 | Kikuchi et al. |

(Continued)

FOREIGN PATENT DOCUMENTS

| JP | 57-005386 A | 1/1982 |
| JP | 2005-167066 A | 6/2005 |

(Continued)

OTHER PUBLICATIONS

International Search Report dated Jun. 18, 2019 received in PCT/JP2019/014268.

*Primary Examiner* — Colin T. Sakamoto
*Assistant Examiner* — Tommy T Ly
(74) *Attorney, Agent, or Firm* — Scully, Scott, Murphy & Presser, P.C.

(57) ABSTRACT

An ultrasound transducer includes: a flexible board configured to receive and output an electrical signal through a signal line; a plurality of piezoelectric devices that are electrically connected to the board and are aligned in a row, each piezoelectric device being configured to transmit and receive an ultrasound wave; a plurality of leads extending the signal line and protruding from an end portion of the board, each lead being electrically connected to the piezoelectric device in a curved manner; and a plurality of sheets that are arranged to prevent the leads from being in contact with each other, each sheet being provided on the lead and having an insulation property.

5 Claims, 9 Drawing Sheets

(56) References Cited

U.S. PATENT DOCUMENTS

| | | | |
|---|---|---|---|
| 9,919,343 B2 | 3/2018 | Fujimura | |
| 2011/0132879 A1* | 6/2011 | Matsumoto | B23K 1/0056 |
| | | | 219/76.1 |
| 2015/0011891 A1* | 1/2015 | Yamada | A61B 8/4494 |
| | | | 600/459 |
| 2019/0117188 A1 | 4/2019 | Wakabayashi | |

FOREIGN PATENT DOCUMENTS

| | | |
|---|---|---|
| JP | 2010-272178 A | 12/2010 |
| JP | 2012-150872 A | 8/2012 |
| JP | 2013-211074 A | 10/2013 |
| WO | 2016/080119 A1 | 5/2016 |
| WO | 2017/199861 A1 | 11/2017 |

* cited by examiner

ALIGNMENT DIRECTION OF PIEZOELECTRIC DEVICES

FIG.11

ALIGNMENT DIRECTION OF PIEZOELECTRIC DEVICES

FIG.12

ALIGNMENT DIRECTION OF PIEZOELECTRIC DEVICES

FIG.13

ALIGNMENT DIRECTION OF PIEZOELECTRIC DEVICES

ULTRASOUND TRANSDUCER, ULTRASOUND ENDOSCOPE, AND MANUFACTURING METHOD OF ULTRASOUND TRANSDUCER

CROSS-REFERENCE TO RELATED APPLICATION

This application is a continuation of International Application No. PCT/JP2019/014268, filed on Mar. 29, 2019, the entire contents of which are incorporated herein by reference.

BACKGROUND

1. Technical Field

The present disclosure relates to an ultrasound transducer, an ultrasound endoscope, and a manufacturing method of an ultrasound transducer.

2. Related Art

In an ultrasound endoscope including an insertion portion to be inserted into a subject, ultrasound waves that are transmitted and received from an ultrasound transducer arranged at a distal end of the insertion portion have been used to observe characteristics of a living tissue or a material, which is a subject of observation. Specifically, information relating to characteristics of the subject of observation can be acquired by subjecting an ultrasound echo received from the ultrasound transducer to predetermined signal processing by an ultrasound imaging device that constitutes the ultrasound endoscope.

The ultrasound transducer includes plural piezoelectric devices that convert an electrical pulse signal into an ultrasound pulse to emit to the subject of observation, and that converts an ultrasound echo reflected on the subject of observation into an electrical echo signal to output. For example, the plural piezoelectric devices are aligned along a predetermined direction, and by electronically switching piezoelectric devices to be involved in transmission and reception, an ultrasound echo is acquired from the subject of observation.

As a type of the ultrasound transducer, a convex type, a linear type, a radial type, and the like of various types of different ultrasound beam transmission/reception directions have been known. Out of these types, a convex ultrasound transducer have plural piezoelectric devices arranged along a curved surface, and each of them emits an ultrasound beam in a radial direction of the curved surface.

International Publication Pamphlet No. WO2016/080119 discloses that a piezoelectric array is formed by arranging plural piezoelectric devices on a flat plate, and that after bending the piezoelectric device array into an arc shape, plural wirings protruded from a distal end of an arc portion included in a flexible board and the respective piezoelectric devices forming the piezoelectric device array are electrically connected, to manufacture a convex ultrasound transducer.

Moreover, International Publication Pamphlet No. WO2016/080119 discloses that a holding member that holds the respective wirings at an interval smaller than an arrangement interval of the piezoelectric devices is arranged transversely at a middle position between the flexible board of each of the wirings and the piezoelectric device, to prevent the plural wirings from coming in contact with one another during a work of electrically connecting the plural wirings and the plural piezoelectric devices.

SUMMARY

In some embodiments, an ultrasound transducer includes: a flexible board configured to receive and output an electrical signal through a signal line; a plurality of piezoelectric devices that are electrically connected to the board and are aligned in a row, each piezoelectric device being configured to transmit and receive an ultrasound wave; a plurality of leads extending the signal line and protruding from an end portion of the board, each lead being electrically connected to the piezoelectric device in a curved manner; and a plurality of sheets that are arranged to prevent the leads from being in contact with each other, each sheet being provided on the lead and having an insulation property.

In some embodiments, an ultrasound endoscope includes an insertion portion configured to be inserted into a subject, the insertion portion having a distal end at which the ultrasound transducer is arranged.

In some embodiments, provided is a manufacturing method of an ultrasound transducer configured to transmit and receive an ultrasound wave. The method includes: pressing distal end portions of a plurality of leads to a plurality of piezoelectric devices such that the plurality of leads are curved, each lead protruding from a distal end of a board and having a sheet arranged at a part of the lead, the plurality of piezoelectric devices being aligned at predetermined intervals; electrically connecting the plurality of piezoelectric devices and the plurality of leads; and joining the distal end portions of the respective leads and the respective piezoelectric devices with a joint material.

The above and other features, advantages and technical and industrial significance of this invention will be better understood by reading the following detailed description of presently preferred embodiments of the disclosure, when considered in connection with the accompanying drawings.

DETAILED DESCRIPTION

Hereinafter, forms to implement the disclosure (hereinafter, embodiments) will be explained with reference to the drawings. The embodiments explained in the following are not intended to limit the disclosure. Furthermore, like reference signs are assigned to like parts in the description throughout the drawings.

First Embodiment

Figure 1:
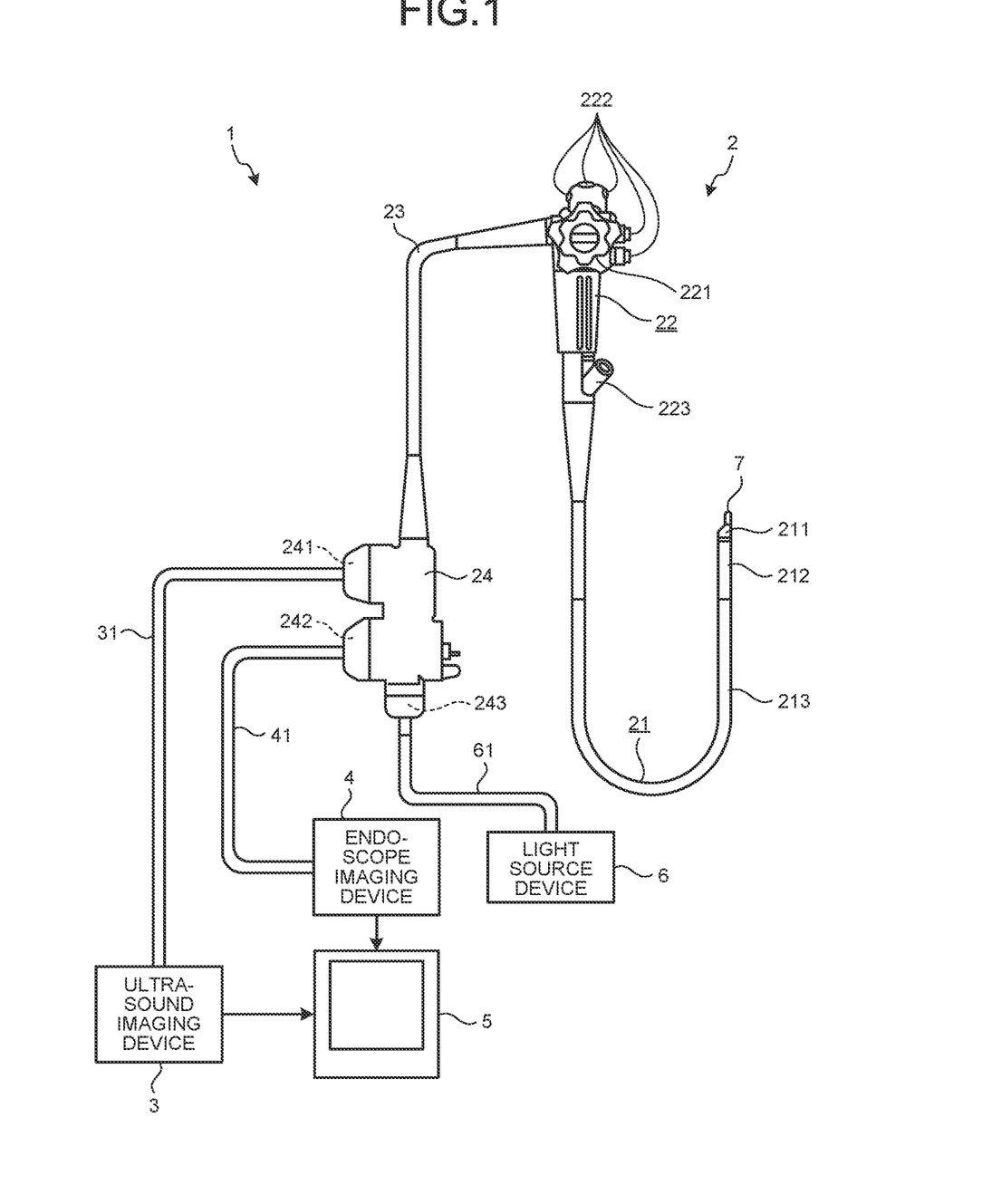
FIG. 1 is a diagram schematically illustrating an endoscope system according to a first embodiment.

FIG. 1 is a diagram schematically illustrating an endoscope system according to a first embodiment. An endoscope system 1 is a system to perform ultrasound diagnosis of an inside of a subject, such as human, by using an ultrasound endoscope. This endoscope system 1 includes an ultrasound endoscope 2, an ultrasound imaging device 3, an endoscope imaging device 4, a display device 5, and a light source device 6 as illustrated in FIG. 1.

The ultrasound endoscope 2 converts an electrical pulse received from the ultrasound imaging device 3 into an ultrasound pulse, to irradiate to the subject by an ultrasound transducer arranged at its distal end portion, and converts an ultrasound echo reflected on the subject into an electrical echo signal that renders it by variation of voltage, to output it.

The ultrasound endoscope 2 normally includes an imaging optical system and an imaging device, is inserted into digestive tracts (esophagus, stomach, duodenum, large intestine) or respiratory organs (trachea, bronchus) of a subject, and is capable of imaging any or those digestive tracts or respiratory organs. Moreover, it is capable of imaging peripheral organs thereof (pancreas, gallbladder, bile duct, biliary tract, lymph node, mediastinal organ, blood vessel, and the like) by using ultrasound waves. Furthermore, the ultrasound endoscope 2 includes a light guide that guide illumination light to illuminate a subject at the time of optical imaging. This light guide has a distal end portion reaching a distal end of an insertion portion to be inserted into the subject of the ultrasound endoscope 2, and a proximal end connected to the light source device 6 that generates the illumination light.

The ultrasound endoscope 2 includes an insertion portion 21, an operating portion 22, a universal cord 23, and a connector 24 as illustrated in FIG. 1. The insertion portion 21 is a portion to be inserted into the subject. This insertion portion 21 is arranged at a distal end side as illustrated in FIG. 1, and includes a distal end portion 211 that is rigid and that holds a convex ultrasound transducer 7, a bendable portion 212 that is formed to be bendable, and that is connected to a proximal end side of the distal end portion 211, and a flexible tube portion 213 that is connected to a proximal end side of the bendable portion 212, and that has flexibility. Inside the insertion portion 21, although specific illustration is omitted, a light guide to transmit the illumination light supplied from the light source device 6, and plural signal cables to transmit various kinds of signals are routed, and an instrument channel to insert a treatment tool therein, and the like are formed.

The operating portion 22 is a portion connected to a proximal end side of the insertion portion 21, and to accept various kinds of operations from a user, such as a doctor. This operating portion 22 includes an operating knob 221 to operate bending of the bendable portion 212, and plural operating members 222 to perform various kinds of operations as illustrated in FIG. 1. Moreover, in the operating portion 22, an instrument channel port 223 that communicates with the instrument channel, and that is to insert a treatment tool into the instrument channel is formed.

The universal cord 23 is a cable that extends from the operating portion 22, and in which plural signal cables to transmit various kinds of signals, and an optical fiber to transmit the illumination light supplied from the light source device 6, and the like are arranged.

The connector 24 is arranged at a distal end of the universal cord 23. The connector 24 includes a first connector portion 241 to which an ultrasound cable 31 is connected, a second connector portion 242 to which a video cable 41 is connected, and a third connector 243 to which an optical fiber cable 61 is connected.

The ultrasound imaging device 3 is electrically connected to the ultrasound endoscope 2 through the ultrasound cable 31 (refer to FIG. 1), outputs a pulse signal to the ultrasound endoscope 2 through the ultrasound cable 31, and receives an echo signal from the ultrasound endoscope 2. The ultrasound imaging device 3 generates an ultrasound image by subjecting the echo signal to predetermined processing.

The endoscope imaging device 4 is electrically connected to the ultrasound endoscope 2 through the video cable 41 (refer to FIG. 1), and receives an image signal from the ultrasound endoscope 2 through the video cable 41. The endoscope imaging device 4 generates an endoscope image by subjecting the image signal to predetermined processing.

The display device 5 is formed by using a liquid crystal or an organic electro luminescence (EL) panel, a projector, a cathode ray tube (CRT), or the like, and displays the ultrasound image generated by the ultrasound imaging device 3, the endoscope image generated by the endoscope imaging device 4, and the like.

The light source device 6 is connected to the ultrasound endoscope 2 through the optical fiber cable 61 (refer to FIG. 1), and supplies the illumination light to illuminate an inside of the subject through the optical fiber cable 61 to the ultrasound endoscope 2.

Figure 2:
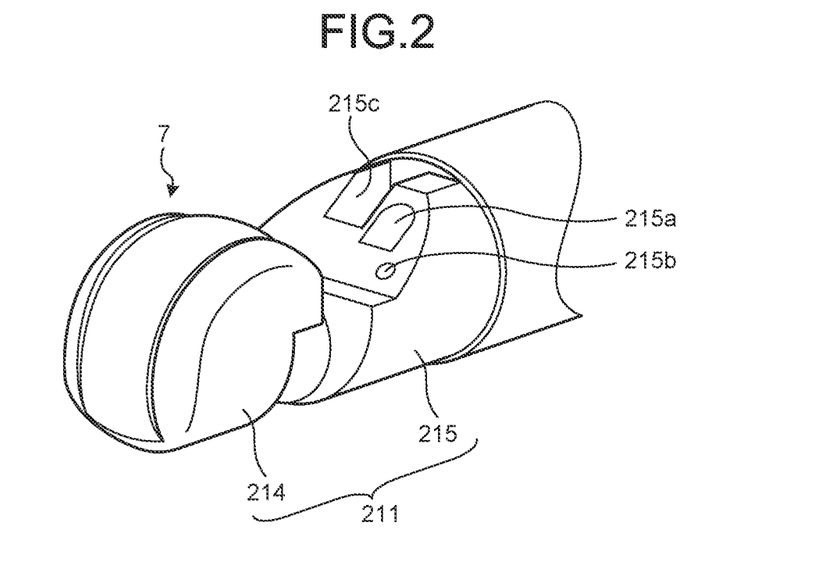
FIG. 2 is a perspective view schematically illustrating a distal end configuration of an insertion portion of an ultrasound endoscope according to the first embodiment.

FIG. 2 is a perspective view schematically illustrating a distal end configuration of the insertion portion of the ultrasound endoscope according to the first embodiment. As illustrated in FIG. 2, the distal end portion 211 includes an ultrasound transducer module 214 that holds the ultrasound transducer 7, an object lens 215a that constitutes a part of the imaging optical system, and that is to take in light from outside, and an endoscope module 215 that has an illumination lens 215b to collect the illumination light to emit to the outside. In the endoscope module 215, an instrument channel outlet 215c that communicates with the instrument channel formed inside the insertion portion 21, and through which a treatment tool is projected from the distal end of the insertion portion 21 is formed. The instrument channel is formed such that a portion near an end portion connected to the instrument channel outlet 215c is inclined relative to a longitudinal axis of the insertion portion 21, and is arranged to project the treatment tool in an inclined direction relative to the longitudinal axis from the instrument channel outlet 215c. The longitudinal axis herein is an axis along a direction of length of the insertion portion 21. While the axial direction of the bendable portion 212 and the flexible tube portion 213 varies depending on a position in the bendable portion 212 and the flexible tube portion 213, the longitudinal axis of the rigid distal end portion 211 is an axis of a fixed linear axis.

Figure 3:
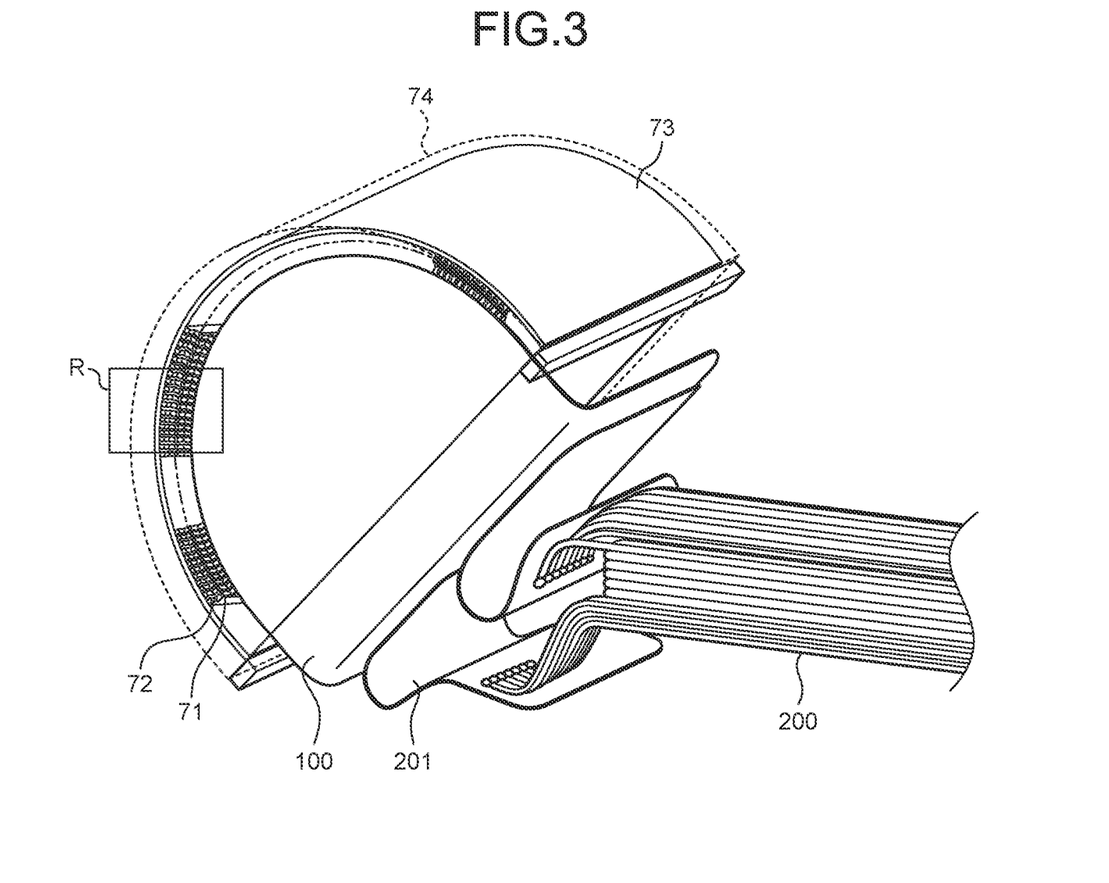
FIG. 3 is a perspective view schematically illustrating a configuration of an ultrasound transducer module according to the first embodiment.
Figure 4:
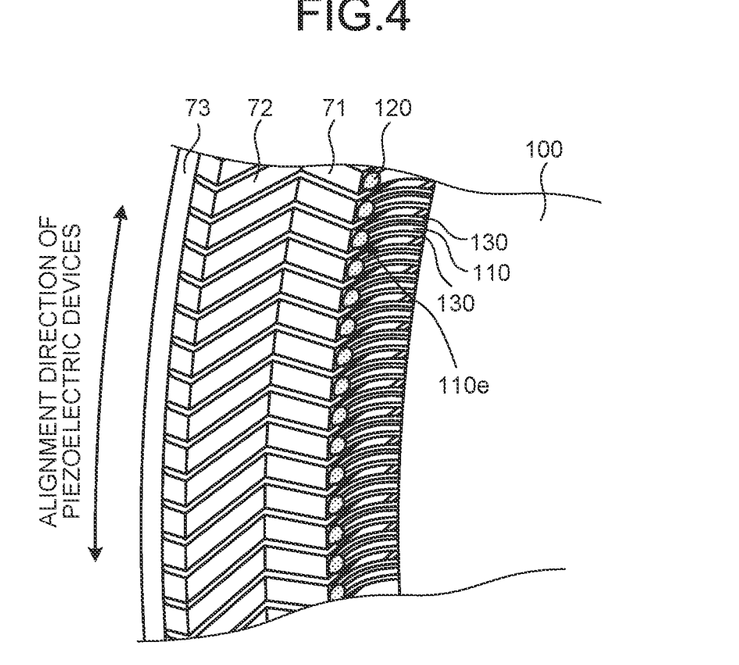
FIG. 4 is a diagram explaining a configuration of a region R of the ultrasound transducer module illustrated in FIG. 3.

Subsequently, a configuration of the ultrasound transducer 7 arranged at the distal end of the insertion portion 21 will be explained. FIG. 3 is a perspective view schematically illustrating a configuration of the ultrasound transducer module 214 according to the first embodiment. FIG. 4 is a diagram explaining a configuration of a region R of the ultrasound transducer module 214 illustrated in FIG. 3.

As illustrated in FIG. 3, in the ultrasound transducer 7, a piezoelectric device array in which plural piezoelectric devices 71 are aligned at predetermined intervals in a row in a curved manner along an outer surface that is a curved surface of the ultrasound transducer 7 is formed. The ultrasound transducer 7 is a convex ultrasound transducer that electronically scans by electronically switching the piezoelectric devices 71 to be involved in transmission and reception, and by delaying transmission and reception of the respective piezoelectric devices.

The ultrasound transducer 7 includes plural piezoelectric devices 71 arranged such that longitudinal directions of the piezoelectric devices 71 are aligned, a first acoustic-matching layer 72 arranged on the piezoelectric devices 71 on an outer surface side of the ultrasound transducer 7, and a second acoustic-matching layer 73 that are arranged on the first acoustic-matching layer 72 on an opposite side to a side in contact with the piezoelectric devices 71, and an acoustic lens 74 that is arranged on the second acoustic-matching layer 73 on an opposite side to a side in contact with the first acoustic-matching layer 72. On an opposite side to a side of the piezoelectric devices 71 in contact with the first acoustic-matching layer 72, a backing material not illustrated is arranged. The backing material is made by using epoxy resin in which a material having a high attenuation factor, for example, a filler such as alumina or zirconia is dispersed, or rubber in which the filler described above is dispersed, and attenuates unnecessary ultrasound vibrations caused by operations of the piezoelectric devices 71.

The piezoelectric device 71 converts an electrical pulse into an acoustic pulse to irradiate to the subject, and converts an ultrasound echo reflected on the subject into an electrical echo signal that renders it by variation of voltage, to output it. In the piezoelectric device 71, for example, a signal input/output electrode not illustrated is arranged on a surface on a backing material side, and a first ground electrode not illustrated for grounding is arranged on a surface on a side closer to the first acoustic-matching layer 72 of the piezoelectric device 71. The respective electrodes are formed by using a metal material or a resin material having an electrical conductivity.

The first acoustic-matching layer 72 and the second acoustic-matching layer 73 matches an acoustic impedance of the piezoelectric device 71 and an acoustic impedance of a subject of observation to transmit ultrasound waves efficiently between the piezoelectric device 71 and the subject of observation. In the first acoustic-matching layer 72, a second ground electrode not illustrated that is electrically connected to the first ground electrode of the piezoelectric device 71 is arranged. The piezoelectric device 71 is grounded to an outside through the first ground electrode and the second ground electrode.

The acoustic lens 74 covers outer surfaces of the first acoustic-matching layer 72 and the second acoustic-matching layer 73, and constitutes an outer surface of the ultrasound transducer 7. The acoustic lens 74 is formed by using silicone, polymethylpentene, epoxy resin, polyetherimide, and the like, and a surface on one side thereof is formed in a convex shape or a concave shape to have a function of narrowing an ultrasound wave, and emits an ultrasound wave that has passed through the second acoustic-matching layer 73 to an outside, or takes in an ultrasound echo from an outside.

The ultrasound transducer 7 irradiates ultrasound waves to the subject of observation with the piezoelectric device 71 vibrating when a pulse signal is input thereto, through the first acoustic-matching layer 72, the second acoustic-matching layer 73, and the acoustic lens 74. At this time, in the piezoelectric device 71, on the opposite side to a side on which the first acoustic-matching layer 72, the second acoustic-matching layer 73, and the acoustic lens 74 are arranged, unnecessary ultrasound vibrations from the piezoelectric devices 71 are attenuated by the backing material. Moreover, ultrasound waves reflected on the subject of observation is transmitted to the piezoelectric device 71 through the acoustic lens 74, the second acoustic-matching layer 73, and the first acoustic-matching layer 72. By the transmitted ultrasound waves, the piezoelectric device 71 vibrates, and the piezoelectric device 71 converts the vibration into an electrical echo signal, to output to the ultrasound imaging device 3 through a flying lead 110 (refer to FIG. 4) that is a wiring described later, as the echo signal.

The ultrasound transducer module 214 includes a relay board 100 that relays electrical connection between the ultrasound transducer 7 and plural signal lines 200 that constitute a part of a route to electrically connect the ultrasound transducer module 214 and the ultrasound imaging device 3. The relay board 100 is a flexible printed circuit (FPC) held by the ultrasound transducer 7 on a side portion of the ultrasound transducer 7. The relay board 100 corresponds to a board, and is electrically connected to the signal lines 200 through a relay board 201. The relay board 100 is formed by providing a wiring pattern on a substrate made from polyimide. Moreover, the relay board 100 is electrically connected to the plural piezoelectric devices 71 by the plural flying leads 110 protruded from a distal end of the relay board 100. The relay board 100 has the distal end from which the flying leads 110 are protruded in an arc shape along the alignment of the piezoelectric devices 71.

In FIG. 4, the flying lead 110 is a lead that is made by using a conductive material, such as copper, or an alloy, a chief constituent of which is copper. The respective flying leads 110 arranged in a state of protruding from the distal end of the relay board 100 are electrically connected to the respective piezoelectric devices 71 in a state of being curved in a convex manner toward the piezoelectric devices 71. A distal end portion 110e that is an end portion of the flying lead 110 on a side being electrically connected to the piezoelectric devices 71 and the piezoelectric device 71 are joined by a solder 120 that is a joint material. Moreover, at a part of the respective flying leads 110, an insulation material 130 that is a flat-shaped sheet having an insulation property is arranged. In the present embodiment, the insulation material 130 is manufactured using the same material as the relay board 100, and the insulation material 130 and the relay board 100 may be arranged integrally, or separately. Furthermore, the insulation material 130 may be manufactured by using a material different from that of the relay board 100.

In the explanation of the first embodiment below, out of any adjacent sets of the flying lead 110 and the piezoelectric device 71, one (a first lead and a first piezoelectric device) may be denoted by adding an index "A" to the reference sign, and the other one (a second lead and a second piezoelectric device) may be denoted by adding an index "B" to the reference sign. Moreover, when the one and the other one of the adjacent sets of the flying lead 110 and the piezoelectric device 71 are not distinguished from each other, the indexes "A" and "B" are omitted.

Figure 5:
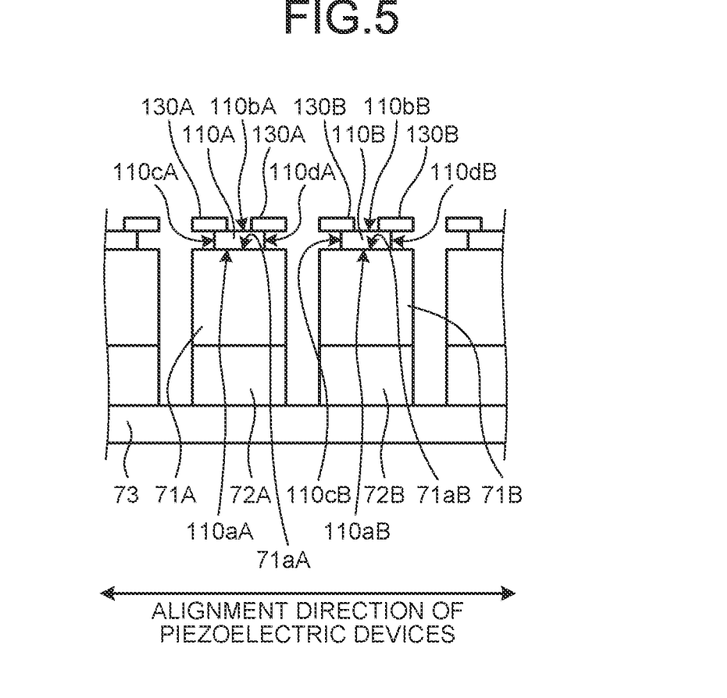
FIG. 5 is a diagram illustrating an arrangement position of an insulation material on a flying lead in the first embodiment.

FIG. 5 is a diagram illustrating an arrangement position of the insulation material 130 on the flying lead 110 in the first embodiment. In the first embodiment, the flying lead 110 is in a flat plate shape, and has a lower surface 110a that is a surface facing the piezoelectric device 71 (surface being in contact with the piezoelectric device 71), an upper surface 110b that is an opposite surface to the lower surface 110a, and side surfaces 110c, 110d that are two surfaces intersecting the lower surface 110a and the upper surface 110b, the side surfaces 110c, 110d being positioned in the an alignment direction of the piezoelectric devices, as illustrated in FIG. 5. Moreover, at edges of the upper surface 110b of the flying lead 110 on both sides in the alignment direction of the piezoelectric devices, the insulation materials 130 are arranged throughout a longitudinal direction of the flying lead 110. Furthermore, a part of the insulation material 130 in the alignment direction of the piezoelectric devices is protruded from the upper surface 110b. In the first embodiment, a sheet having no insulation property may be used in place of the insulation material 130.

Figure 6:
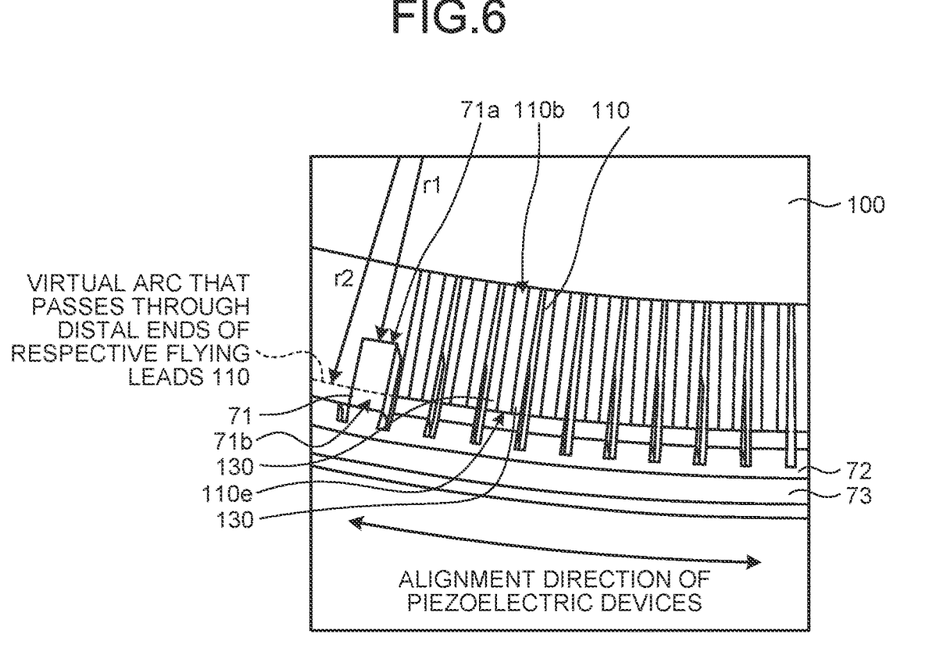
FIG. 6 is a perspective view of a state before the flying lead and a piezoelectric device are electrically connected.
Figure 7:
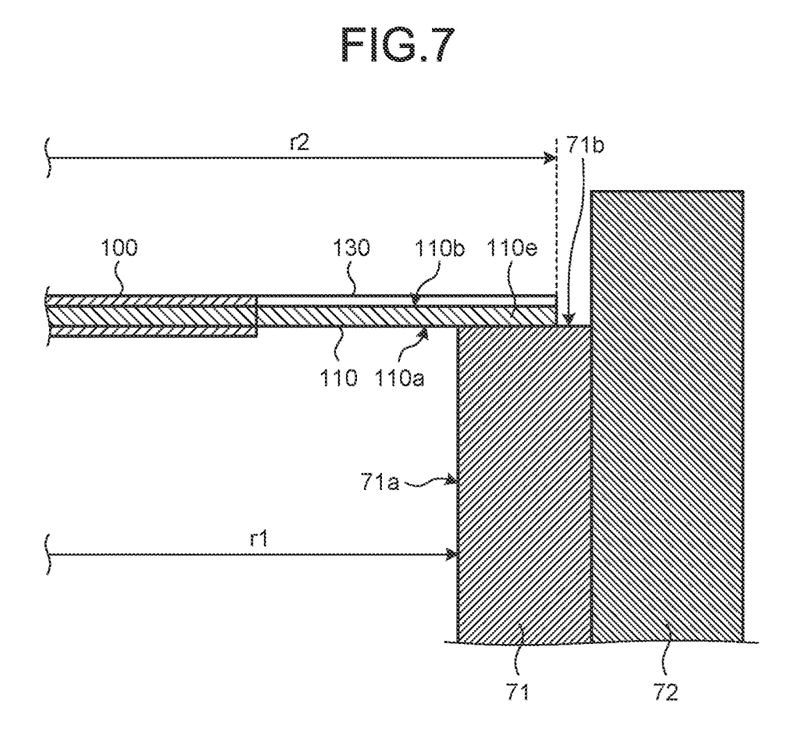
FIG. 7 is a partial cross-section of the ultrasound transducer module, which is taken along a plane that is perpendicular to an alignment direction of the piezoelectric devices and that passes through the flying leads in a state before the flying leads and the piezoelectric devices are electrically connected to each other.
Figure 8:
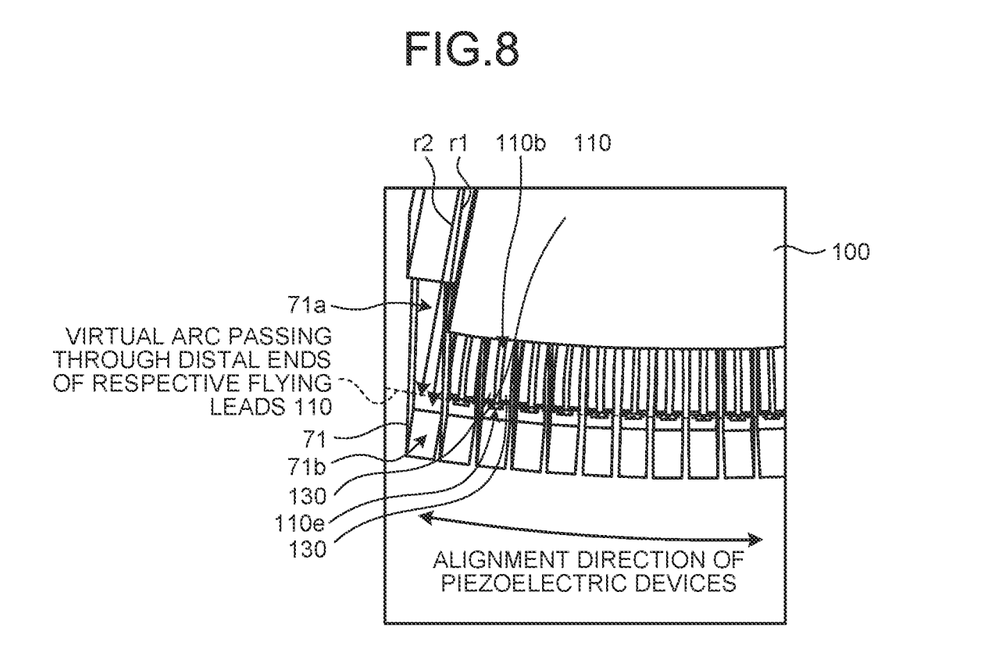
FIG. 8 is a perspective view in a state in which the flying lead and the piezoelectric devices are electrically connected to each other.
Figure 9:
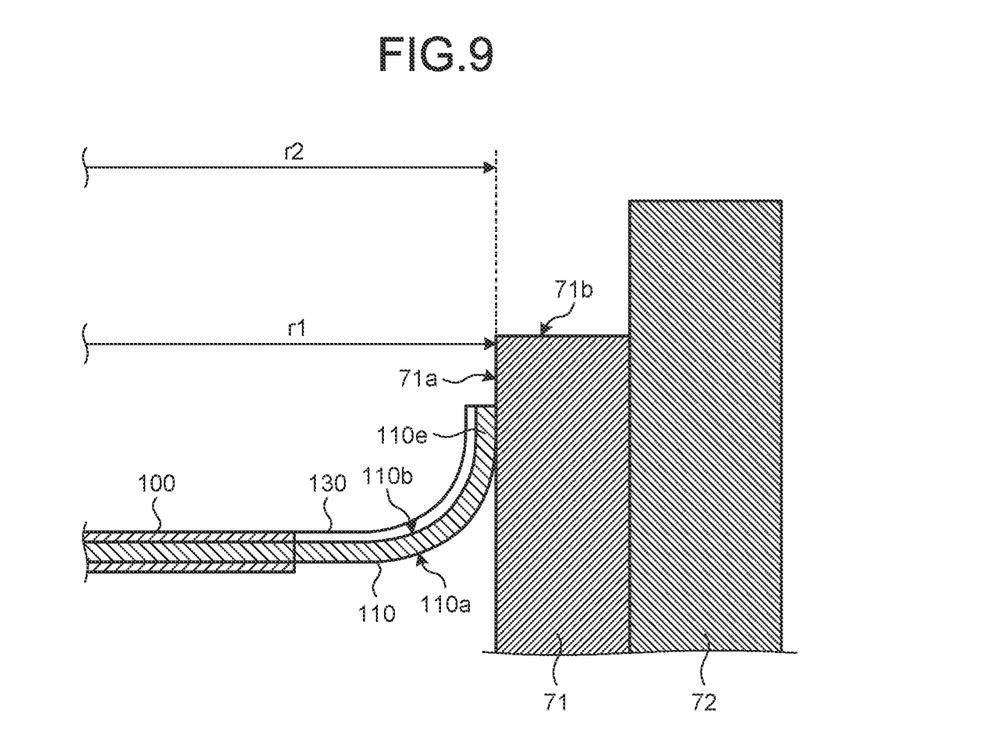
FIG. 9 is a partial cross-section of the ultrasound transducer module, which is taken along a plane that is perpendicular to the alignment direction of the piezoelectric devices and that passes through the flying lead in a state in which the flying lead and the piezoelectric devices are electrically connected to each other.

Next, a manufacturing method for manufacturing the ultrasound transducer module 214 will be explained. FIG. 6 is a perspective view of a state before the flying lead 110 and the piezoelectric device 71 are electrically connected. FIG. 7 is a partial cross-section of the ultrasound transducer module 214, which is taken along a plane that is perpendicular to an alignment direction of the piezoelectric devices 71 and that passes through the flying leads 110 in a state before the flying leads 110 and the piezoelectric devices 71 are electrically connected to each other. FIG. 8 is a perspective view in a state in which the flying leads 110 and the piezoelectric devices 71 are electrically connected to each other. FIG. 9 is a partial cross-section of the ultrasound transducer module 214, which is taken along a plane that is perpendicular to the alignment direction of the piezoelectric devices 71 and that passes through the flying leads 110 in a state in which the flying leads 110 and the piezoelectric devices 71 are electrically connected to each other.

When manufacturing the ultrasound transducer module 214, first, the first acoustic-matching layer 72 and the second acoustic-matching layer 73 are stacked on the piezoelectric devices 71. Next, as illustrated in FIG. 6 and FIG. 7, the distal end portions 110e of the flying leads 110 that extend straight and protrude from the distal end of the relay board 100 are positioned on end surfaces 71b of the piezoelectric devices 71 corresponding to the respective fling leads 110. At this time, a curvature radius r2 of a virtual arc passing through the distal end of the respective flying leads 110 coaxial to an inner diameter center of the piezoelectric array is larger than an inner diameter r1 of the piezoelectric array. As illustrated in FIG. 8 and FIG. 9, the flying lead 110 is brought down together with the relay board 100 while pressing the lower surface 110a at the distal end portion 110e of the flying lead 110 to an inner surface 71a of the piezoelectric device 71, and the flying lead 110 is curved in a convex manner toward the piezoelectric device 71. At this time, the curvature radius r2 of the virtual arc passing through the respective distal ends of the flying leads 110 is smaller than the inner diameter r1 of the piezoelectric device array. Thereafter, the flying leads 110 and the piezoelectric devices 71 are joined by the solder 120 as illustrated in FIG. 4 in a state in which the lower surface 110a at the distal end portion 110e of the flying lead 110 and the inner surface 71a of the piezoelectric device 71 are in contact with each other.

The lower surface 110a at the distal end portion 110e of the flying lead 110 may be formed in a tapered shape. Thus, a contact area when the lower surface 110a at the distal end portion 110e of the flying lead 110 and the inner surface 71a of the piezoelectric device 71 are brought into contact by bending the flying lead 110 in a convex manner toward the piezoelectric device 71 can be increased to be larger than a case of not arranging the tapered shape. As the contact area increases, a friction force acting on a contact portion of the lower surface 110a at the distal end portion 110e of the flying lead 110 and the inner surface 71a of the piezoelectric device 71 increases, and displacement of the flying lead 110 with respect to the piezoelectric device 71 can be suppressed. Moreover, when the contact area increases, a joint area of the flying lead 110 and the piezoelectric device 71 by the solder 120 can be increased and, therefore, the joint strength can be improved.

after the flying leads 110 and the piezoelectric devices 71 are joined by the solder 120, the backing material is filled on the opposite side to the side of the first acoustic-matching layer 72 of the piezoelectric devices 71, and the acoustic lens 74 is attached. Thus, the ultrasound transducer module 214 is manufactured.

In the first embodiment, by providing the insulation material 130 at the edge of the upper surface 110b of the flying lead 110, the rigidity of the flying lead 110 can be increased compared to a case without the insulation material 130. It is thus possible to suppress the flying lead 110 curved in a direction different from an intended bending direction when the flying lead 110 is curved toward the intended bending direction to make it convex toward the piezoelectric device 71 side by pressing the lower surface 110a at the distal end portion 110e of the flying lead 110 to the inner surface 71a of the piezoelectric device 71. Therefore, it is possible to suppress the flying lead 110 to be short-circuited through the other piezoelectric device 71 as a result of the flying lead 110 being curved in the alignment direction of the piezoelectric devices that is a different direction from the intended bending direction, to contact the other piezoelectric device 71 that has been in contact with the other flying lead 110.

Moreover, out of the adjacent flying leads 110A and 110B as illustrated in FIG. 5, for example, even if the flying lead 110A is displaced toward the flying lead 110B, the insulation material 130 of the flying lead 110A contacts the insulation material 130B of the flying lead 110B adjacent to each other in the alignment direction of the piezoelectric devices. Thus, a short circuit caused by the flying lead 110A and the flying lead 110B becoming in contact with each other, or a short circuit of the flying leads 110A, 110B through the piezoelectric device 71B can be suppressed.

First Modification

Figure 10:
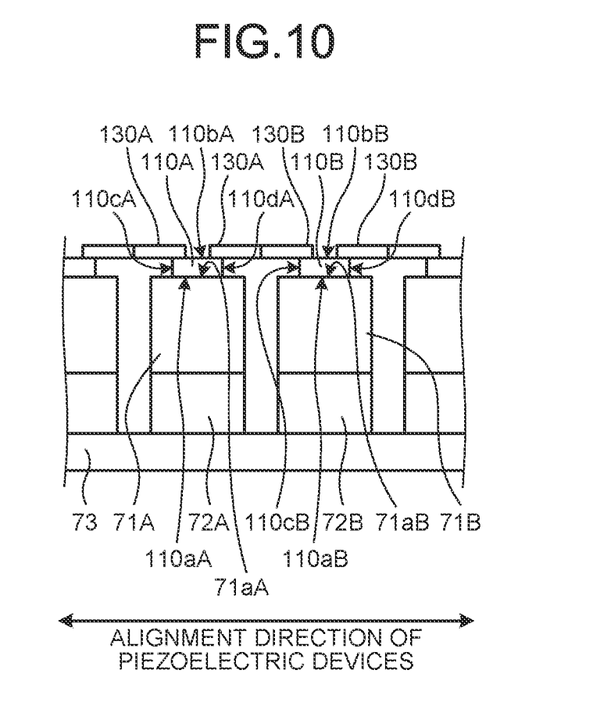
FIG. 10 is a diagram illustrating an arrangement position of an insulation material on the flying lead in a first modification.

FIG. 10 is a diagram illustrating an arrangement position of the insulation material 130 on the flying lead 110 in a first modification. In the first modification, the insulation material 130 is arranged at the edge in the respective upper surfaces 110b of the flying leads 110, and the adjacent insulation materials 130 are arranged to be in contact with each other in the alignment direction of the piezoelectric devices.

For example, as illustrated in FIG. 10, out of the adjacent flying leads 110A, 110B, the insulation material 130A arranged on the upper surface 110b of the flying lead 110A and the insulation material 130 arranged on the upper surface 110b of the flying lead 110B are in contact with each other in the alignment direction of the piezoelectric devices. Thus, displacement of the flying leads 110A, 110B in the alignment direction of the piezoelectric devices can be suppressed, and a short circuit caused by the flying leads 110A, 110B becoming into contact with each other, or a short circuit of the flying leads 110A, 110B through the piezoelectric device 71A or the piezoelectric device 71B can be suppressed.

Second Embodiment

Next, a second embodiment will be explained. In explanation of the second embodiment below, identical reference signs are assigned to components similar to those of the first embodiment, and detailed explanation thereof will be omitted or simplified.

Figure 11:
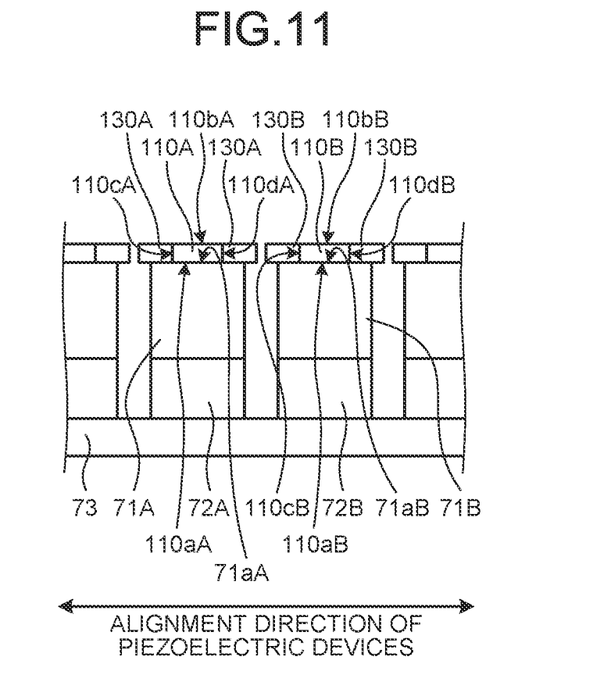
FIG. 11 is a diagram illustrating an arrangement position of the insulation material on the flying lead in a second modification.

FIG. 11 is a diagram illustrating an arrangement position of the insulation material 130 on the flying lead 110 in the second modification. In the second embodiment, as illustrated in FIG. 11, the flying lead 110 is in a flat plate shape similarly to the first embodiment, and has the lower surface 110a that is a surface facing the piezoelectric device 71, the upper surface 110b that is an opposite surface to the lower surface 110b, and the side surfaces 110c, 110d that are two surfaces intersecting the lower surface 110a and the upper surface 110b, the side surfaces 110c, 110d being positioned in the alignment direction of the piezoelectric devices. Furthermore, as illustrated in FIG. 11, on the side surfaces 110c, 110d of the flying lead 110, the insulation materials 130 are respectively arranged throughout the longitudinal direction of the flying lead. In the second embodiment, a sheet having no insulation property may be used in place of the insulation material 130.

In the second embodiment, by providing the insulation materials 130 on the side surfaces 110c, 110d of the flying lead 110, the rigidity of the flying lead 110 can be improved compared to the case without the insulation material 130. Thus, when manufacturing the ultrasound transducer module 214, it is thus possible to suppress the flying lead 110 curved in a direction different from an intended bending direction when the flying lead 110 is curved toward the intended bending direction to make it convex toward the piezoelectric device 71 side by pressing the lower surface 110a at the distal end portion 110e of the flying lead 110 to the inner surface 71a of the piezoelectric device 71. Therefore, it is possible to suppress the flying lead 110 to be short-circuited through the other piezoelectric device 71 as a result of the flying lead 110 being curved in the alignment direction of the piezoelectric devices that is a different direction from the intended bending direction, to contact the other piezoelectric device 71 that has been in contact with the other flying lead 110.

Moreover, out of the adjacent flying leads 110A and 110B as illustrated in FIG. 11, for example, even if the flying lead 110A is displaced toward the flying lead 110B, the insulation material 130 of the flying lead 110A contacts the insulation material 130B of the flying lead 110B adjacent to each other in the alignment direction of the piezoelectric devices. Thus, a short circuit caused by the flying lead 110A and the flying lead 110B becoming in contact with each other, or a short circuit of the flying leads 110A, 110B through the piezoelectric device 71B can be suppressed.

Second Modification

Figure 12:
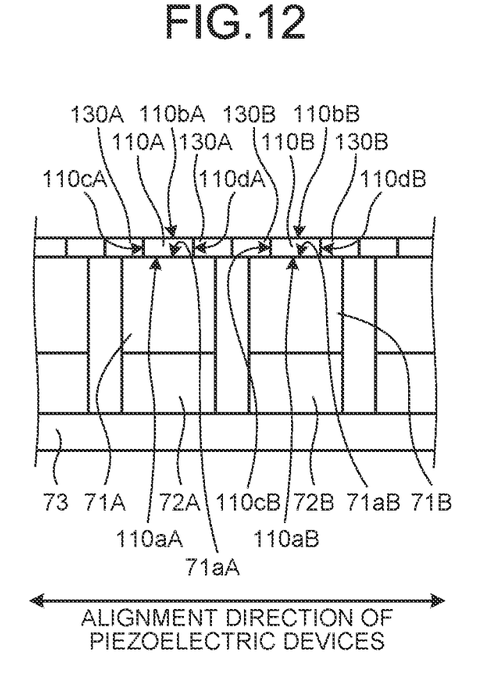
FIG. 12 is a diagram illustrating an arrangement position of an insulation material on the flying lead in the second modification.

FIG. 12 is a diagram illustrating an arrangement position of the insulating material 130 on the flying lead 110 in the second modification. In the second modification, the adjacent insulation materials 130 are arranged to be in contact with each other in the alignment direction of the piezoelectric devices, and the insulation material 130 is arranged on the side surfaces 110c, 110d of the flying leads 110.

For example, as illustrated in FIG. 12, out of the adjacent flying leads 110A, 110B, the insulation material 130A arranged on a side surface 110dA of the flying lead 110A and the insulation material 130 arranged on a side surface 110cB of the flying lead 110B are in contact with each other in the alignment direction of the piezoelectric devices. Thus, displacement of the flying leads 110A, 110B in the alignment direction of the piezoelectric devices can be suppressed, and a short circuit caused by the flying leads 110A, 110B becoming into contact with each other, or a short circuit of the flying leads 110A, 110B through the piezoelectric device 71A or the piezoelectric device 71B can be suppressed.

Figure 13:
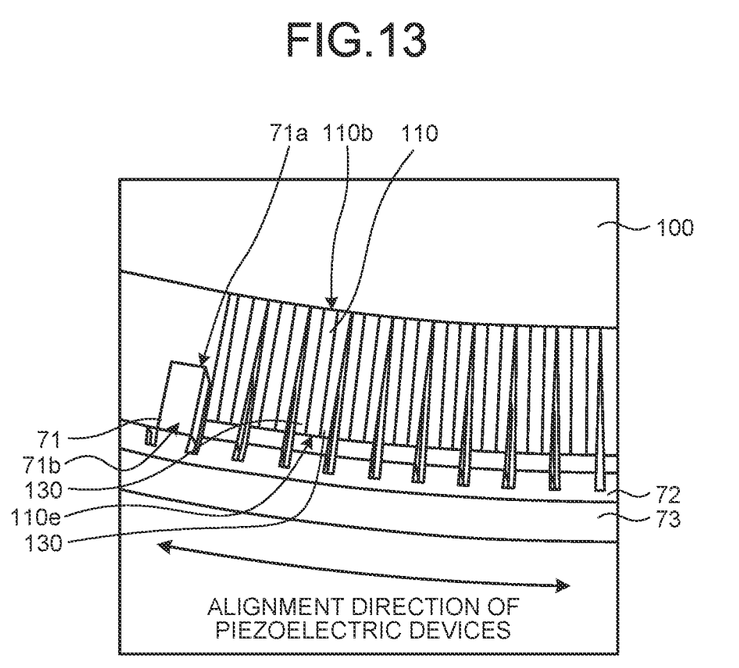
FIG. 13 is a perspective view illustrating a state before the flying lead is curved in the second modification.
Figure 14:
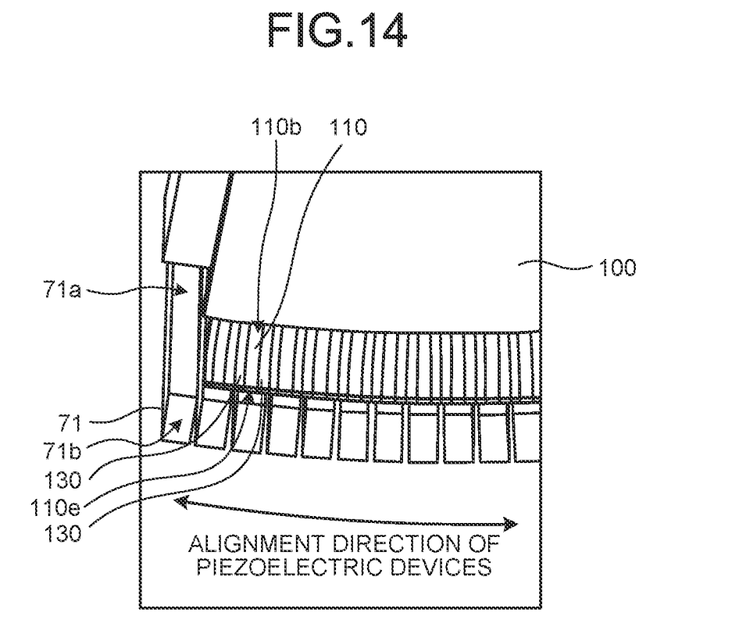
FIG. 14 is a perspective view illustrating a state after the flying lead is curved in the second modification.

Moreover, as illustrated in FIG. 13, before the flying lead 110 is curved in a convex manner toward the piezoelectric device 71, a gap is formed between the insulation materials 130 adjacent in the alignment direction of the piezoelectric devices. Furthermore, as illustrated in FIG. 14, after the flying lead 110 is curved in a convex manner toward the piezoelectric device 71, at least a part of the gap between the insulation materials 130 adjacent to each other disappears, and the adjacent insulation materials 130 come into contact with each other.

In the second modification, the gap before the flying lead 110 is curved is arranged to have such a shape and a width that at least a part of the gap disappears when the flying lead 110 is curved in a convex manner toward the piezoelectric device 71 in accordance with a predetermined degree of curve of the flying lead 110. For example, as illustrated in FIG. 13, the gap is in a triangular shape in a plan view, and a width thereof becomes wider toward the distal end portion 110e of the flying lead 110 from the relay board 100 side in the longitudinal direction of the flying lead.

Third Embodiment

Next, a third embodiment will be explained. In explanation of the third embodiment below, identical reference signs are assigned to components similar to those of the first embodiment, and detailed explanation will be omitted or simplified.

Figure 15:
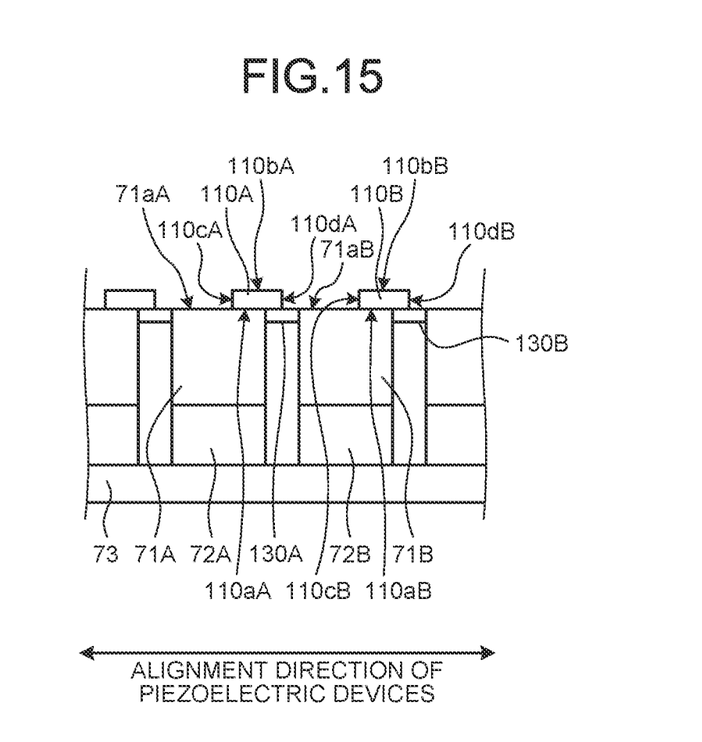
FIG. 15 is a diagram illustrating an arrangement position of an insulation material on the flying lead in a third embodiment.

FIG. 15 is a diagram illustrating an arrangement position of the insulation material 130 on the flying lead 110 in the third embodiment. In the third embodiment, the flying lead 110 is in a flat plate shape similarly to the first embodiment, and has a lower surface 110a that is a surface facing the piezoelectric device 71, the upper surface 110b that is an opposite surface to the lower surface 110a, and the side surfaces 110c, 110d that are two surfaces intersecting the lower surface 110a and the upper surface 110b, the side surfaces 110c, 110d being positioned in the an alignment direction of the piezoelectric devices as illustrated in FIG. 15. Moreover, at an edge of the upper surface 110b of the flying lead 110 on one side in the alignment direction of the piezoelectric devices, the insulation material 130 is arranged throughout a longitudinal direction of the flying lead 110. Furthermore, a part of the insulation material 130 in the alignment direction of the piezoelectric devices is protruded from the lower surface 110a.

Moreover, in the third embodiment, when the flying lead 110 is curved in a convex manner toward the piezoelectric device 71 to electrically connect the flying lead 110 and the piezoelectric device 71, the insulation material 130 is fit in a gap between the adjacent piezoelectric devices 71. For example, as illustrated in FIG. 15, in the gap between the piezoelectric devices 71A and 71B adjacent to each other, the insulation material 130A arranged at the edge of a lower surface 110aA of the flying lead 110A is fit. Thus, movement of the flying lead 110A toward the alignment direction of the piezoelectric devices is restricted by the insulation material 130A and the piezoelectric devices 71A, 71B becoming into contact with each other. Therefore, displacement of the flying lead 110A relative to the piezoelectric device 71A in the alignment direction of the piezoelectric devices can be suppressed, and a short circuit caused by the flying lead 110A and the flying lead 110B becoming into contact with each other, or a short circuit of the flying leads 110A, 110B through the piezoelectric device 71B can be suppressed.

Fourth Embodiment

Next, a fourth embodiment of the disclosure will be explained. In explanation of the fourth embodiment below, identical reference signs are assigned components similar to those of the first embodiment, and detailed explanation will be omitted or simplified.

Figure 16:
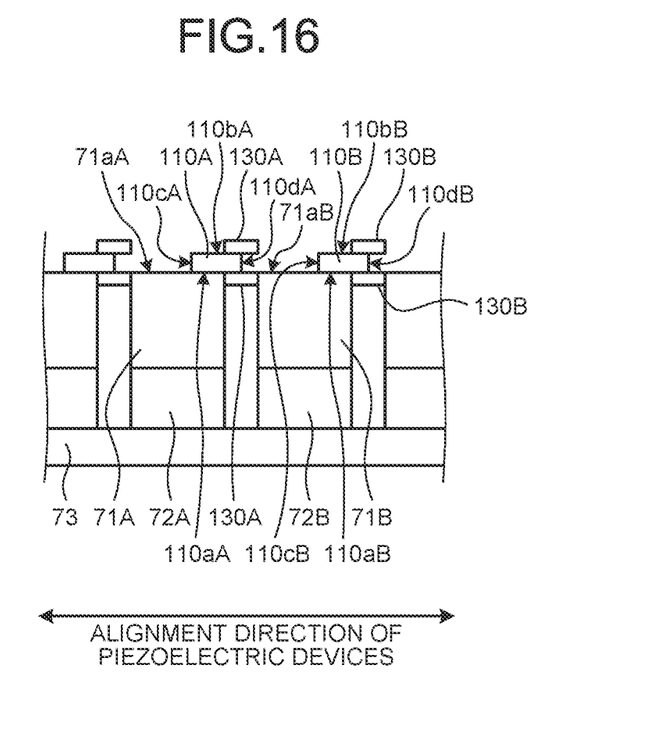
FIG. 16 is a diagram illustrating an arrangement position of a first insulating member and a second insulating member on a flying lead in a fourth embodiment.

FIG. 16 is a diagram illustrating an arrangement position of a first insulation material 131 and a second insulation material 132 on the flying lead 110 in the fourth embodiment. In the fourth embodiment, as illustrated in FIG. 16, the flying lead 110 is in a flat plate shape similarly to the first embodiment, and has a lower surface 110a that is a surface facing the piezoelectric device 71, the upper surface 110b that is an opposite surface to the lower surface 110a, and the side surfaces 110c, 110d that are two surfaces intersecting the lower surface 110a and the upper surface 110b, the side surfaces 110c, 110d being positioned in the an alignment direction of the piezoelectric devices. At an edge of the lower surface 110a of the flying lead 110 on one side in the alignment direction of the piezoelectric devices, a first insulation material 131 is arranged throughout the longitudinal direction of the flying lead. Furthermore, a part of the first insulation material 131 in the alignment direction of the piezoelectric devices is protruded from the lower surface 110a. Moreover, at an edge of the upper surface 110b of the flying lead 110 on one side in the alignment direction of the piezoelectric devices, a second insulation material 132 is arranged throughout the longitudinal direction of the flying lead. Furthermore, a part of the second insulation material 132 in the alignment direction of the piezoelectric devices is protruded from the upper surface 110b.

In the fourth embodiment, the first insulation material 131 and the second insulation material 132 are manufactured by using the same material as the relay board 100, and the first insulation material 131, the second insulation material 132, and the relay board 100 may be arranged integrally, or separately. Furthermore, the first insulation material 131 and the second insulation material 132 may be manufactured by using a material different from that of the relay board 100.

In the fourth embodiment, when the flying lead 110 is curved in a convex manner toward the piezoelectric device 71 to electrically connecting the flying lead 110 and the piezoelectric device 71, the first insulation material 131 is fit in a gap between the adjacent piezoelectric devices 71. For example, as illustrated in FIG. 16, in a gap between the adjacent piezoelectric devices 71A and 71B, the first insulation material 131A of the flying lead 110A is fit. Thus, displacement of the flying lead 110A in the alignment direction of the piezoelectric devices can be suppressed, and a short circuit caused by the flying lead 110A and the flying lead 110B becoming into contact with each other, or a short circuit of the flying leads 110A, 110B through the piezoelectric device 71B can be suppressed.

Moreover, in the fourth embodiment, by arranging the second insulation material 132 at the edge of the upper surface 110b of the flying lead 110, a flow of melted solder can be stopped by the first insulation material 131 when the distal end portion 110e of the flying lead 110 and the piezoelectric device 71 are joined with solder. For example, as illustrated in FIG. 16, by stopping melted solder by a second insulation material 132A of the flying lead 110A when the distal end portion 110e of the flying lead 110A and the piezoelectric device 71A are joined with solder in the adjacent flying leads 110A and 110B, it is possible to suppress the melted solder to flow into the flying lead 110B side. Thus, a short circuit of the flying leads 110A, 110B through the solder can be suppressed.

In the respective embodiments described above, shapes of the insulation material 130, the first insulation material 131, and the second insulation material 132 are not limited to a planar shape, but may be in any shape to improve the rigidity of the flying lead 110 so that bending of the flying lead 110 in a direction different from an intended bending direction can be suppressed.

Moreover, in the respective embodiments described above, the flying lead 110 may be curved in a convex shape toward an opposite side to the piezoelectric device 71 side.

A ultrasound transducer, an ultrasound endoscope, and a manufacturing method of an ultrasound transducer are useful for preventing a short circuit of a lead caused through a piezoelectric device.

An ultrasound transducer, an ultrasound endoscope, and a manufacturing method of an ultrasound transducer according to the disclosure produce an effect of preventing a lead from being short-circuited through a piezoelectric device.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising:
a flexible board comprising a plurality of signal lines configured to receive and output an electrical signal;
a plurality of piezoelectric devices, each piezoelectric device of the plurality of piezoelectric devices being electrically connected to a respective signal line of the plurality of signal lines, the plurality of piezoelectric devices being aligned in an alignment direction, each piezoelectric device being configured to transmit and receive an ultrasound wave;
a lead extending from each of the plurality of signal lines, each lead protruding from an end portion of the board, each lead electrically connecting the respective signal line to a respective piezoelectric device of the plurality of piezoelectric devices; and
a plurality of sheets, at least a portion of each sheet of the plurality of sheets being arranged on and between adjacent leads in the alignment direction, each sheet having an electrical insulation property;
wherein the board includes an arc portion with an arc shape,
each lead is arranged to protrude from a distal end of the arc portion,
the plurality of piezoelectric devices are aligned along the arc portion, and
surfaces of at least two adjacent sheets of the plurality of sheets are in contact with each other, the surfaces intersecting the alignment direction of the plurality of piezoelectric devices.

2. The ultrasound transducer according to claim 1, wherein each lead is curved.

3. An ultrasound endoscope comprising
an insertion portion configured to be inserted into a subject, the insertion portion having a distal end at which the ultrasound transducer according to claim 1 is arranged.

4. An ultrasound transducer comprising:
a flexible board comprising a plurality of signal lines configured to receive and output an electrical signal;
a plurality of piezoelectric devices, each piezoelectric device of the plurality of piezoelectric devices being electrically connected to a respective signal line of the plurality of signal lines, the plurality of piezoelectric devices being aligned in an alignment direction, each piezoelectric device being configured to transmit and receive an ultrasound wave;
a lead extending from each of the plurality of signal lines, each lead protruding from an end portion of the board, each lead electrically connecting the respective signal line to a respective piezoelectric device of the plurality of piezoelectric devices; and
a plurality of sheets, at least a portion of each sheet of the plurality of sheets being arranged on and between adjacent leads in the alignment direction, each sheet having an electrical insulation property;
wherein each lead has a flat plate shape,
each sheet is made of a sheet-shaped insulation material arranged on a surface of one of the adjacent leads, the surface facing the respective piezoelectric device, and
each sheet is positioned between adjacent piezoelectric devices.

5. An ultrasound transducer comprising:
a flexible board comprising a plurality of signal lines configured to receive and output an electrical signal;
a plurality of piezoelectric devices, each piezoelectric device of the plurality of piezoelectric devices being electrically connected to a respective signal line of the plurality of signal lines, the plurality of piezoelectric devices being aligned in an alignment direction, each piezoelectric device being configured to transmit and receive an ultrasound wave;
a lead extending from each of the plurality of signal lines, each lead protruding from an end portion of the board, each lead electrically connecting the respective signal line to a respective piezoelectric device of the plurality of piezoelectric devices; and
a plurality of sheets, at least a portion of each sheet of the plurality of sheets being arranged on and between adjacent leads in the alignment direction, each sheet having an electrical insulation property;
wherein each lead has a flat plate shape,
each sheet comprises first and second sheets, the first sheet and the second sheet are made of a sheet-shaped insulation material, the first sheet being arranged on a part of a second surface of each lead and the second sheet being arranged on a part of a third surface of each lead, the second surface facing the piezoelectric device, the third surface being opposite to the second surface, and
the first sheet is positioned between adjacent piezoelectric devices.

* * * * *